United States Patent [19]

Jones et al.

[11] Patent Number: 4,463,005

[45] Date of Patent: Jul. 31, 1984

[54] BICYCLIC GUANIDINES

[75] Inventors: Derrick J. Jones; Keith Oldham, both of Cheshire, United Kingdom

[73] Assignee: Imperial Chemical Industries PLC, London, England

[21] Appl. No.: 356,802

[22] Filed: Mar. 10, 1982

[30] Foreign Application Priority Data

Mar. 18, 1981 [GB] United Kingdom ................ 8108408

[51] Int. Cl.³ ................ C07D 401/06; C07D 413/06; A61K 31/505

[52] U.S. Cl. .................................... 424/249; 424/250; 424/251; 424/263; 424/268; 424/270; 424/272; 424/273 R; 544/212; 544/296; 544/331; 544/357; 544/405; 546/276; 546/277; 546/278; 546/281; 548/128; 548/131; 548/202; 548/235; 548/255; 548/269; 548/336

[58] Field of Search ............... 544/212, 331, 405, 296, 544/357; 546/276, 277, 278, 281; 424/249, 251, 250, 263

[56] References Cited

U.S. PATENT DOCUMENTS

| 4,242,350 | 12/1980 | Yellin et al. | 424/263 |
|---|---|---|---|
| 4,242,351 | 12/1980 | Yellin et al. | 424/263 |
| 4,302,464 | 11/1981 | LaMattina et al. | 424/263 |
| 4,315,009 | 2/1982 | Jones et al. | 424/263 |
| 4,342,765 | 8/1982 | Jones et al. | 424/263 |
| 4,362,728 | 12/1982 | Yellin | 424/249 |

FOREIGN PATENT DOCUMENTS 33094 1/1981 European Pat. Off. ............ 424/263

*Primary Examiner*—Robert Gerstl
*Attorney, Agent, or Firm*—Cushman, Darby & Cushman

[57] ABSTRACT

The invention relates to bicyclic derivatives which are histamine H-2 antagonists and which inhibit gastric acid secretion. According to the invention there is provided a guanidine derivative of the formula I:

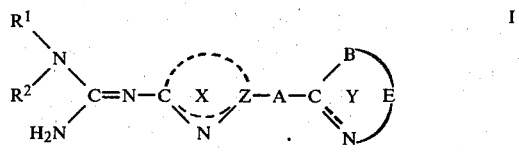

in which $R^1$ and $R^2$, same or different, are hydrogen or 1–10C alkyl, 3–8C cycloalkyl or 4–14C cycloalkylalkyl, each alkyl, cycloalkyl or cycloalkylalkyl optionally carrying one or more F, Cl or Br atoms, provided that one of $R^1$ and $R^2$ is halogen substituted, or $R^2$ is hydrogen and $R^1$ is $R^3$-E-W in which W is 2–6C alkylene optionally substituted by 1 or 2 1–4C alkyls, E is O, S, SO, $SO_2$ or $NR^4$ in which $R^4$ is H or 1–6C alkyl, $R^3$ is H or 1–6C alkyl optionally substituted by 1 or 2 1–4C alkyls, or $R^3$ and $R^4$ are joined to form a pyrrolidine, piperidine, morpholine, piperazine or N-methylpiperazine ring, or $R^2$ is H and $R^1$ is H, 1–10C alkyl, 3–8C cycloalkyl, 4–14C cycloalkylalkyl, 3–6C alkenyl, 3–6C alkynyl, 1–6C alkanoyl, 6–10C aryl, 7–11C aralkyl or 7–11C aroyl; ring X is a heterocyclic ring as defined in the specification; A is phenylene or 5–7C cycloalkylene, or a 1–8 C alkylene into which is optionally inserted one or two groups; ring Y is a heterocyclic ring described in the specification: and the pharmaceutically-acceptable acid-addition salts thereof. Manufacturing processes and pharmaceutical compositions are also described.

10 Claims, No Drawings

BICYCLIC GUANIDINES

This invention relates to bicyclic derivatives which are histamine H-2 antagonists and which inhibit gastric acid secretion.

It is postulated that the physiologically-active compound histamine, which occurs naturally within the animal body, is able to combine, in the course of exerting its activity, with certain specific receptors of which there are at least two distinct and separate types. The first has been named the H-1 receptor (Ash and Schild, Brit. J. Pharmac. 1966, 27, 427) and the action of histamine at this receptor is blocked (antagonised) by classical "antihistamine" drugs such as mepyramine. The second histamine receptor has been named the H-2 receptor (Black et al., Nature, 1972, 236, 385) and the action of histamine at this receptor is blocked by drugs such as cimetidine. It is known that one of the results of the blockade of the action of histamine at the H-2 receptor is the inhibition of the secretion of gastric acid and a compound which possesses this ability is therefore useful in the treatment of peptic ulcers and other conditions caused or exacerbated by gastric acidity.

In UK Patent Application No. 2001624 and European Patent Publications Nos. 6286, 6679, 30092 and 45155 there are described histamine H-2 receptor antagonists which are guanidino heterocycles carrying a side chain to the end of which is attached a modified guanidine residue. It has now been discovered that if this modified guanidine is replaced by a nitrogen heterocycle linked via a carbon atom there are obtained potent histamine H-2 receptor antagonists.

According to the invention there is provided a guanidine derivative of the formula I:

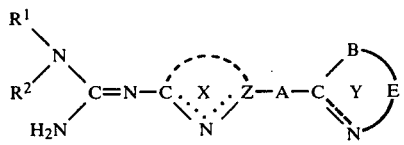

I in which $R^1$ and $R^2$, which may be the same or different, are hydrogen atoms or branched or unbranched 1-10C alkyl, 3-8C cycloalkyl or 4-14C cycloalkylalkyl radicals, each alkyl, cycloalkyl or cycloalkylalkyl radical being optionally substituted by one or more halogen atoms selected from fluorine, chlorine and bromine atoms, provided that at least one of $R^1$ and $R^2$ is a halogen-substituted alkyl, cycloalkyl or cycloalkylalkyl radical, and provided that there is no halogen substituent on the carbon atom of the alkyl, cycloalkyl or cycloalkylalkyl radical which is directly attached to the nitrogen atom, or $R^2$ is a hydrogen atom and $-R^1$ is a radical of the formula II:

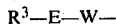 $R^3-E-W-$     II in which W is an unbranched 2-6C alkylene chain which is optionally substituted by one or two 1-4C alkyl radicals, E is an oxygen or sulphur atom, a sulphinyl or sulphonyl radical, or a radical of the formula $NR^4$ in which $R^4$ is a hydrogen atom or a 1-6C alkyl radical, $R^3$ is a hydrogen atom or an unbranched 1-6C alkyl radical which is optionally substituted by one or two 1-4C alkyl radicals, or $R^3$ and $R^4$ are joined to form, together with the nitrogen atom to which they are attached, a pyrrolidine, piperidine, morpholine, piperazine or N-methylpiperazine ring, or $R^2$ is a hydrogen atom and $R^1$ is a hydrogen atom or a 1-10C alkyl, 3-8C cycloalkyl, 4-14C cycloalkylalkyl, 3-6C alkenyl, 3-6C alkynyl, 1-6C alkanoyl, 6-10C aryl, 7-11C arylalkyl or 7-11C aroyl radical, the aryl, arylalkyl and aroyl radicals being optionally substituted on the aryl ring by one or two substituents selected from fluorine, chlorine and bromine atoms and 1-6C alkyl, 1-6C alkoxy, 1-6C alkylthio, trifluoromethyl, hydroxy and amino radicals; in ring X the dotted line is a double bond on one side of the nitrogen atom and Z is a carbon or nitrogen atom such that ring X is a 5- or 6-membered aromatic heterocyclic ring which contains at least one nitrogen atom and may optionally contain one or two additional hetero atoms selected from oxygen, nitrogen and sulphur atoms, which heterocyclic ring may, where possible, carry one or two optional substituents, the optional substituents on ring X being selected from fluorine, chlorine and bromine atoms and 1-6C alkyl, 1-6C alkoxy, 1-6C alkylthio, trifluoromethyl, hydroxy and amino radicals; A is a 1-8C alkylene chain which is optionally substituted by one or two 1-3C alkyl radicals and into which is optionally inserted, as part of the backbone of the chain, an NH or a 1-6C N-alkyl radical or one or two groups selected from oxygen and sulphur atoms and cis and trans vinylene, ethynylene, phenylene and 5-7C alkylene radicals, provided that no two insertions selected from oxygen and sulphur atoms and NH and N-alkyl radicals are directly attached one to the other, and provided tnat when an optional insertion is made in chain A wnich results in the inserted group being directly attached to ring Y the inserted group is other than an NH or N-alkyl radical, or A is a 5-7C cycloalkylene radical or phenylene radical; in ring Y the dashed line represents an optional double bond, B is an oxygen or sulphur atom or a CH, $CH_2$ or CO radical and E is a chain of two or three atoms or radicals selected from oxygen, sulphur and nitrogen atoms and CH, $CH_2$, SO and $SO_2$ radicals such that ring Y is a 5- or 6-membered heterocyclic ring, which may be saturated, partially unsaturated or fully unsaturated, and such that to ring Y is optionally fused a benzene ring, ring Y being optionally substituted on a nitrogen atom by a 1-6C alkyl radical or on a carbon atom by a halogen atom or a hydroxy, nitro, amino, 1-6C alkylamino, 2-8C dialkylamino, cyano, carboxy, carbamoyl, sulphamoyl, 1-6C alkyl or 1-6C alkanesulphonyl radical and the benzene ring optionally fused to ring Y being optionally substituted by one or two substituents selected from halogen atoms and 1-6C alkyl, 1-6C alkoxy, 1-6C alkylthio, hydroxy and amino radicals:

and the pharmaceutically-acceptable acid-addition salts thereof.

It is to be understood that, in the above formula I and throughout this specification, although the double bonds in both groups attached to ring X have been inserted in particular positions, other tautomeric forms are possible, and this invention includes such tautomeric forms within its scope, both in terms of the compounds of the invention and in terms of the manufacturing processes. Similarly, when ring Y is substituted by a hydroxy radical, that radical may exist in the tautomeric keto form. It is also to be understood that when A is or contains a cycloalkylene radical the groups attached to this radical may be in the cis or trans configuration. When A is or contains a cycloalkylene radical and/or when A is an alkylene chain substituted by one or two alkyl radicals, the compound of the formula I will, in most instances, contain at least one asymmetric centre. In such cases the compound of the formula I will therefore exist in at least two enantiomeric forms, the precise number being determined by the number of asymmetric centres. The biological activity, as hereinafter defined, of these enantiomeric forms may differ, and it is therefore to be understood that this invention encompasses the racemate of the formula I, including any possible diastereoisomeric forms, and any enantiomeric form which possesses the disclosed biological activity, it being a matter of common general knowledge to one skilled in the art how to separate diastereoisomeric forms and how to separate a racemate into its enantiomers and determine the biological activity of each.

A particular value for $R^1$ or $R^2$ when it is a halogen-substituted alkyl radical is a 2,2,2-trifluoroethyl, 2,2,2-trichloroethyl, 2-chloro-2,2-difluoroethyl, 2,2-dichloro-2-fluoroethyl, 2-bromo-2,2-difluoroethyl, 2,2-dibromo-2-fluoroethyl, 2-fluoroethyl, 2-chloroethyl, 2,2-difluoroethyl, 2,2-dichloroethyl, 2-chloro-2-fluoroethyl, 2-bromo-2-fluoroethyl, 2,2,3,3-tetrafluoropropyl, 2,2,3,3,3-pentafluoropropyl, 1,1,1,3,3,3-hexafluoroisopropyl, 1,3-dichloro-1,1,3,3-tetrafluoroisopropyl, 1-chloro-1,1,3,3,3-pentafluoroisopropyl, 1,3-difluoroisopropyl or 2,2,3,3,4,4,4-heptafluorobutyl radical.

A particular value for $R^1$ or $R^2$ when it is a halogen-substituted cycloalkyl radical is a 2,2,3,3-tetrafluorocyclopropyl, 2-chloro-2,3,3-trifluorocyclopropyl, 2,2-difluorocyclopropyl, 2-chloro-3,3-difluorocyclopropyl, 2,2,3,3,4,4-hexafluorocyclobutyl or 2-chloro-2,3,3,4,4-pentafluorocyclobutyl radical.

A particular value for $R^1$ or $R^2$ when it is a halogen-substituted cycloalkylalkyl radical is a (1,2,2,3,3-pentafluorocyclopropyl)methyl, (2-chloro-1,2,3,3-tetrafluorocyclopropyl)methyl, (1,2,2,3,3,4,4-heptafluorocyclobutyl)methyl or [2-chloro-1,2,3,3,4,4-hexafluorocyclobutyl]methyl radical.

A particular value for $R^1$ and $R^2$ when it is an alkyl radical is a methyl, ethyl, propyl, isopropyl or butyl radical.

A particular value for $R^1$ or $R^2$ when it is a cycloalkyl radical is a cyclopropyl or cyclobutyl radical.

A particular value for $R^1$ or $R^2$ when it is a cycloalkylalkyl radical is a cyclopropylmethyl or cyclobutylmethyl radical.

A particular value for the optional substituent on W is a methyl radical.

A particular value for $R^3$ is a hydrogen atom or a methyl radical.

A particular value for $R^4$ is a hydrogen atom or a methyl radical.

A particular value for the radical of the formula II is a 2-methoxyethyl, 2-hydroxyethyl, 2-methylthioethyl or 2-dimethylaminoethyl radical.

When $R^2$ is a hydrogen atom a particular value for $R^1$ is a hydrogen atom or a methyl, ethyl, propyl, isopropyl, butyl, cyclohexyl, cyclohexylmethyl, allyl, propargyl, acetyl, phenyl, benzyl or benzoyl radical, the phenyl, benzyl and benzoyl radicals being optionally substituted on the phenyl ring by one or two substituents selected from fluorine, chlorine and bromine atoms and methyl, methoxy, methylthio, trifluoromethyl, hydroxy and amino radicals.

A particular value for ring X is an oxazole, thiazole, imidazole, 1,2,4-thiadiazole, 1,2,4-oxadiazole, 1,2,3-triazole, 1,2,4-triazole, pyrazole, pyrazine, pyridine, pyrimidine or 1,3,5-triazine ring.

A particular value for the optional substituent on ring X when it is an alkyl, alkoxy or alkylthio radical is a methyl, methoxy or methylthio radical.

A particular value for —A— is a phenylene, cyclopentylene, cyclohexylene, trimethylene, tetramethylene, pentamethylene, thioethylene, thiotrimethylene, thiotetramethylene, thiopentamethylene, oxyethylene, oxytrimethylene, oxytetramethylene, methylenethiomethylene, methylenethioethylene, methylenethiopropylene, methyleneoxymethylene, methyleneoxyethylene, ethyleneoxyethylene, oxy-2-methylethylene, thiopropylenethiomethylene, tetramethyleneoxy, oxypropyleneoxy, oxyethyleneoxymethylene, oxyethylenethio, oxypropylenethio, iminoethylene, iminopropylene, vinylenepropylene, oxymethylenevinylene, 1,3-phenylene, 1,3-cyclopentylene, methylene-1,4-phenylene, ethyleneoxymethylene-1,4-phenylene, oxy-1,3-phenylenemethylene or thiomethyleneethynylenemethylene radical. These values for —A— are written reading from left to right in formula I such that the first named part of the radical is attached to ring X and the last named part of the radical is attached to ring Y. Thus, for example, when —A— is a thiotrimethylene radical, the compound of the formula I contains the part structure III:

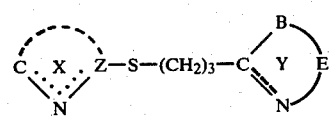

A particular value for the optional substituent on ring Y is a fluorine, chlorine or bromine atom or a hydroxy, nitro, amino, methylamino, dimethylamino, cyano, carboxy, carbamoyl, sulphamoyl, methyl or methanesulphonyl radical.

A particular value for the optional substituent on the benzene ring which is optionally fused to ring Y is 1 or 2 substituents selected from fluorine, chlorine and bromine atoms and methyl, methoxy, methylthio, trifluoromethyl, hydroxy and amino radicals.

A particular value for ring Y is a ring of the formula IV, V, VI, VII, VIII, IX, X, XI, XII, XIII, XIV, XV, XVI or XVII:

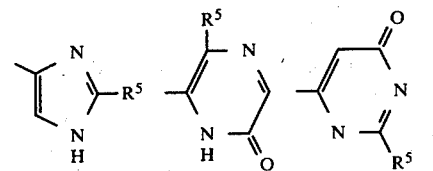

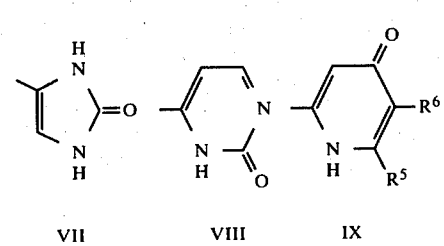

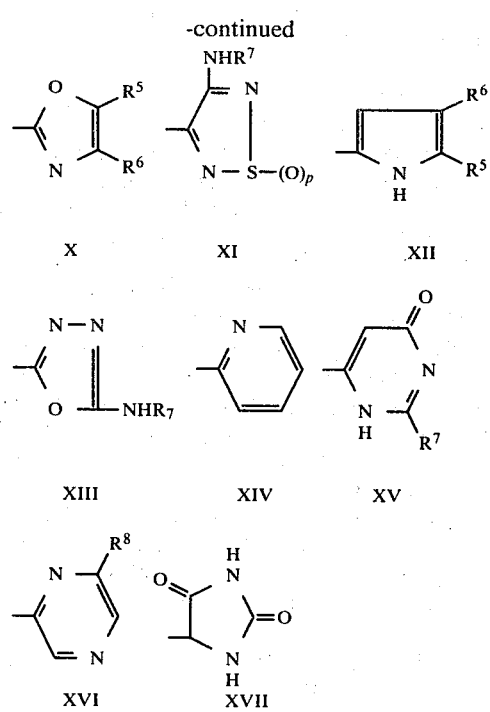

in which $R^5$ is a hydrogen atom or a radical of the formula $NHR^7$, $R^6$ is a hydrogen atom or a cyano, nitro, 2-6C alkoxycarbonyl (for example methoxycarbonyl), carbamoyl, 1-6 alkylcarbamoyl (for example methylcarbamoyl) or 2-8C dialkylcarbamoyl (for example dimethylcarbamoyl)radical, $R^7$ is a hydrogen atom or a 1-6C alkyl (for example a methyl) radical, $R^8$ is a hydrogen or halogen (for example a chlorine or bromine) atom and p is 1 or 2.

The following are eleven preferred features of the guanidine derivative of the formula I. When any one of these features is taken, either singly or in combination, with the other general or particular features of the guanidine derivative listed above there are obtained preferred sub-groups of compounds within the above general definition.

1. Ring Y is of the formula IV, V, VI, VII, VIII, IX, X, XI, XII or XIII in which $R^6$ is a hydrogen atom or a cyano, nitro, methoxycarbonyl, carbamoyl, methylcarbamoyl or dimethylcarbamoyl radical and $R^7$ is a hydrogen atom or a methyl radical.

2. $R^2$ is a hydrogen atom and $R^1$ is a 2,2,2-trifluoroethyl or propyl radical.

3. $R^2$ is a hydrogen atom and $R^1$ is a 2,2,2-trifluoroethyl radical.

4. Ring X carries no optional substitutent.

5. Ring X is a pyrazole ring, or a pyrimidine ring in which A is linked at the 2-position.

6. A is a tetramethylene, pentamethylene, thiotrimethylene, oxyethylene, oxytrimethylene, tetramethyleneoxy or oxytrimethyleneoxy radical.

7. A is a tetramethylene or thiotrimethylene radical.

8. Ring Y is of the formula IV in which $R^5$ is a hydrogen atom or an amino or methylamino radical.

9. Ring X is a pyrimidine ring in which A is linked at the 2-position and A is a tetramethylene or thiotrimethylene radical.

10. Ring X is a pyrazole ring and A is a tetramethylene radical.

11. Ring Y is of the formula IV in which $R^5$ is a hydrogen atom.

Particular compounds of the invention are set out in the Examples. The following is a group of preferred compounds:

4-[4-(4-[2-(2,2,2-trifluoroethyl)guanidino]pyrimid-2-yl)butyl]imidazole (Example 1);
4-[3-(4-[2-(2,2,2-trifluoroethyl)guanidino]pyrimid-2-ylthio)propyl]imidazole (Example 2);
4-[4-(3-[2-(2,2,2-trifluoroethyl)guanidino]pyrazol-1-yl)butyl]imidazole (Example 9);

and the pharmaceutically-acceptable acid-addition salts thereof.

A suitable pharmaceutically-acceptable acid-addition salt of the guanidine derivative of the formula I is, for example, a salt formed with hydrochloric, hydrobromic, phosphoric, sulphuric, acetic, citric or maleic acid.

The guanidine derivative of the invention may be manufactured by methods in which the actual chemical reactions involved are known in themselves. The following processes, $R^1$, $R^2$, A, ring X and ring Y having the meanings stated above, unless indicated otherwise, are therefore provided as further features of the invention.

The process of the invention is characterised by:

(a) construction of the guanidine radical attached to ring X by reaction of the appropriate thiourea, or a 1-6C S-alkyl (e.g. S-methyl) or S-benzyl derivative thereof, or a salt of such a derivative, with the appropriate amine. The guanidine radical in the compound of the formula I contains three nitrogen atoms each of which carries different substituents. The appropriate amine for use in this reaction may therefore be ammonia, an amine of the formula $R^1R^2NH$ or an axine of the formula XVIII:

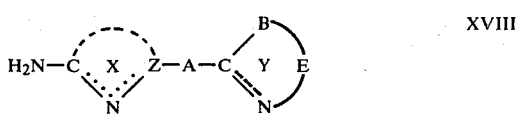

XVIII

The reaction may be conducted using an excess of one of the reactants as a diluent or solvent, or an additional diluent or solvent, for example methanol or ethanol, may be added. In many cases it is advantageous to use a catalyst such as mercuric oxide, lead oxide or sodium hypochlorite. The reaction may be conducted at ambient temperature or it may be accelerated or completed by the application of heat, for example by heating to the boiling point of the diluent or solvent.

(b) for those compounds in which the group inserted into A is an oxygen or sulphur atom or an NH or N-alkyl radical, reaction of a compound of the formula XIX or XX:

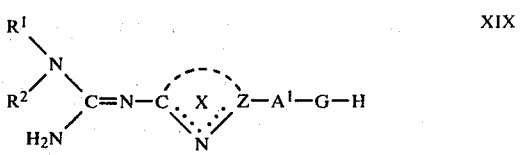

XIX

-continued

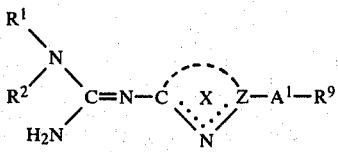

with a compound of the formula XXI or XXII respectively:

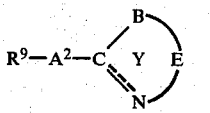

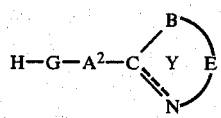

in which G is an oxygen or sulphur atom or an NH or N-alkyl radical, $R^9$ is a displaceable radical and $A^1$ and $A^2$ are fragments of —A—, including direct bonds, and are such that $A^1$—G—$A^2$ falls within the definition of A given above. $R^9$ is, for example, a halogen atom, for example a chlorine, bromine or iodine atom. When $R^9$ is directly attached to ring X may, for example, be a methylsulphinyl or methylsulphonyl radical.

(c) construction of ring Y by reaction of a suitably functionalised carbon atom attached to the end of chain A in a standard heterocyclic ring synthesis. Thus when ring Y is an imidazole ring the carbon atom attached to A is functionalised as a cyano group and is reacted with an isonitrile of the formula XXIII:

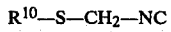

in which $R^{10}$ is a phenyl or p-tolyl radical. The imidazole ring thus formed is then desulphurised, for example with Raney nickel. When ring Y is a 2,5-dihydroxyimidazole ring the carbon atom attached to A is functionalised as an aldehyde, and the ring is formed by reaction with potassium cyanide and ammonium carbonate.

(d) for those compounds in which Z is a nitrogen atom, reaction of a compound of the formula XXIV:

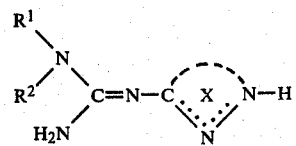

with a compound of the formula XXV:

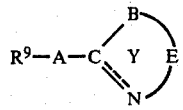

in which $R^9$ is a displaceable radical, $R^9$ is, for example, a halogen atom, for example a chlorine, bromine or iodine atom.

(e) construction of the guanidine radical attached to ring X by reaction of the appropriate cyanamide with the appropriate amine. Since the guanidine radical in the compound of the formula I contains only one unsubstituted nitrogen atom there are two appropriate amines, namely the amine of the formula $R^1R^2NH$ or of the formula XVIII given above.

(f) for those compounds in which ring X is a thiazole ring, reaction of a compound of the formula XXVI:

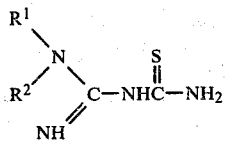

with a compound of the formula XXVII:

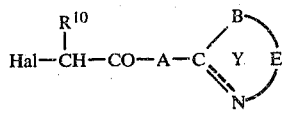

in which Hal is a chlorine or bromine atom and $R^{10}$ is a hydrogen atom or the optional substituent on the thiazole ring. The reaction may be conducted in a diluent or solvent such as acetone and may be accelerated or completed by the application of heat, for example by heating to the boiling point of the diluent or solvent.

When the process of the invention manufactures the compound of the formula I in the form of the free base and an acid-addition salt is required, the compound of the formula I in the free base form is reacted with an acid which affords a pharmaceutically-acceptable anion.

The preparation of the starting materials for use in the processes of the invention may be illustrated by reference to the preparation of the starting material for use in process (c). This starting material may be prepared by separate construction of the two side chains on an appropriate ring X. Thus the left hand side chain may be constructed by reduction of a nitro group to an amino group, reaction of this amino group with an isothiocyanate of the formula $R^1R^2N$—C═S, and finally reaction of the resulting thiourea with ammonia in the presence of mercuric oxide. The method of construction of the right hand side chain may vary depending on the nature of ring X, the nature of the atom in ring X to which A is attached (carbon or nitrogen) and the presence or absence of inserted atoms or groups in chain A. When A contains no inserted group, or the inserted group is a phenylene radical and Z is a carbon atom, it is preferable to construct ring X with the right hand side chain already in place. Thus, for example, when ring X is a pyrimidine ring, it may be formed by reaction of a suitably substituted amidine with 2-chloroacrylonitrile to give the corresponding 4-aminopyrimidine derivative, for example as illustrated in Example 1. When the inserted group in A is a cycloalkylene radical, the chain A may be constructed by a conjugate addition to the corresponding cycloalk-2-enone. When the inserted group in A is a vinylene or ethynylene radical, A may be introduced by formation of the double or triple bond by standard coupling methods. When the inserted group in A is an oxygen or sulphur atom or an NH or N-alkyl radical, the right hand side chain may be built up by a method similar to that in process (b). When Z is a nitrogen atom, the right hand chain may be formed by a method similar to that in process (d), for example as illustrated in Example 9.

The starting material of the formula XVIII for use in process (a) or (e) may be prepared in a similar manner to that described above for the preparation of the right hand side chain in the starting material for process (c). The preparation of this starting material is illustrated in Examples 1 and 2.

The starting materials of the formulae XIX and XX for use in process (b) may be prepared in a similar manner to that described above for the starting material for process (c). The preparation of these starting materials is illustrated in Examples 6 and 8.

The starting materials of the formulae XXI and XXII for use in process (b) and XXV for use in process (d) may be prepared by standard chemical reactions, for example as illustrated in Example 5.

The starting material of the formula XXIV for use in process (d) may be prepared by construction of the guanidine radical on a suitable aminoheterocycle, as previously described.

As noted above, the guanidine derivative of the invention is a histamine H-2 antagonist, inhibits the secretion of gastric acid in warm-blooded animals and is therefore useful in the treatment of peptic ulcers and other conditions caused or exacerbated by gastric acidity, including stress ulcers and gastrointestinal bleeding due to trauma.

The histamine H-2 antagonist activity may be demonstrated on standard tests, for example by the ability of the compound of the formula I to inhibit the histamine-induced uptake of aminopyrine into the acid space of parietal cells.

The aminopyrine test is carried out as follows:

Gastric mucosa from the New Zealand white rabbit is removed from the underlying muscel and washed in Buffer 1 [containing per litre NaCl; (8.007 g.), KCl (0.201 g.), $Na_2HPO_4$ (0.113 g.), $KH_2PO_4$ (0.204 g.), $CaCl_2.2H_2O$ (0.132 g.), $MgCl_2$ (0.101 g.) and glucose (1 g.), adjusted to pH 7.4 with NaOH]. The tissue is finely chopped, suspended in Buffer 1 and washed three times with Buffer 1. The tissue is then suspended in dispersion medium [collagenase (Sigma Chemical Co., Type V; 100 mg.) and bovine serium albumin (Miles Laboratories Ltd., Fraction V; 100 mg.) in Buffer 1 (100 ml.); 50 ml. per 10 g. net weight of tissue] and incubated at 30° C. and pH 7.4 (maintained by continuous monitoring) with stirring under an oxygen atmosphere. After 30 minutes the tissue is allowed to settle and the supernatant liquid is removed. Fresh dispersion medium (50 ml. per 10 g. wet weight of tissue) is added and incubation is continued with the tissue being largely dispersed into glands and whole cells after 40–60 minutes. Any remaining large pieces of tissue are removed by filtration through nylon mesh. The mixture of glands and cells is collected by centrifugation at $200 \times g$. and suspended in Buffer 1 containing 1% bovine serum albumin (Miles Laboratories Ltd., Fraction V). Finally the cells and glands are washed 3 times with Buffer 1 and suspended in Buffer 2 [containing Eagles MEM (500 ml.), Aprotinin (Sigma Chemical Co., 10 mg.) and HEPES (2-[4-(2-hydroxyethyl)piperazin-1-yl]ethanesulphonic acid; 150 mM., 20 ml.) adjusted to pH 7.4 with NaOH; 150 ml. per 10 g. wet weight of tissue]. The tissue suspension is stirred under an oxygen atmosphere at 32° C. for at least 1 hour before use. The tissue suspension is incubated with the test compound and aminopyrine (10 $\mu$M) labelled with $C^{14}$ on the dimethylamino group (0.1 $\mu$Ci/ml.) for 20 minutes. The uptake of the aminopyrine is then stimulated by addition of histamine and the phosphodiesterase inhibitor ICI 63197 (*Biochem. Soc. Special Publication* 1, 1973, pp 127–132) to final concentrations of $10^{-5}$M. and $5 \times 10^{-7}$M. respectively. After 18 minutes the cells/glands are separated from the incubation medium by filtration of the suspension through glass microfibre filters. The cells/glands are quickly (<10 seconds) washed three times with ice-cold Buffer 1. The $C^{14}$ aminopyrine retained by the tissue is measured on a scintillation counter and the degree of inhibition of uptake by the test compound is calculated by reference to a control sample. The concentration of test compound giving 50% inhibition is then calculated graphically from a series of tests run at different concentrations.

All the compounds exemplified in this specification were tested on the aminopyrine test. All gave a 50% inhibition of uptake of aminopyrine at or below a concentration of 3 $\mu$M.

The inhibition of the secretion of gastric acid may be demonstrated in standard tests, for example by the ability of the compound of the formula I, when dosed intravenously, intragastrically or orally, to inhibit the secretion of acidic gastric juice in, for example, rats or dogs provided with denervated fundic pouches, and whose gastric secretion is stimulated by administration of a secretagogue, for example histamine, pentagastrin, bethanechol or food.

The test in rats is carried out as follows:

Female rats (200–230 g.) are anaesthetized by intramuscular administration of urethane (1.5 g./kg.) and the trachea cannulated. A soft tube is passed down the oesophagus into the stomach and secured by a tie in the neck region. A multi-orifice plastic tube (3 mm. diameter) is passed into the antral region of the stomach, via an incision in the duodenum, and tied in place by means of a ligature around the pylorus. Saline (9 g./l. NaCl) is perfused through the stomach via the oesophageal cannula at a rate of 7 ml./minute and collected into beakers from the pyloric outlet over periods of 10 minutes. Acid secretion is stimulated by subcutaneous administration of the specific H-2 agonist dimaprit in a loading dose of 10 mg./kg. followed by an infusion of 30 mg./kg./hour. Acid output is computed by titration of the 10 minutes samples to an end point of pH 6.4 with 20 mM. NaOH. When secretion has reached a plateau (three consecutive readings within 5%) the test compound is administered intravenously via a cannula placed in the left external jugular vein. Secretion is then measured for a further 2 hours. A stock solution of each test compound is prepared (10 mg./ml. in DMSO) and appropriate dilution made with saline to enable injection in a dose volume of 1 ml./kg. (DMSO<2%).

The test in dogs provided with denervated fundic pouches is carried out as follows:

Male beagle dogs (14–22 kg.) are prepared with vagally denervated pouches of the fundic gland area by the method of Rudick et al. (*J. Surg. Res.* 1967, 7, 383). The animals are allowed 4–6 weeks to recover from surgery and a further period of 2–3 months prior to routine use, to allow for table training and standardization of secretory responses. The dogs are starved for 23 hours before use (water ad lib) and during experiments they are lightly restrained in cloth slings. After rinsing the pouch with warm water, histamine is infused subcutaneously at a rate of 10 $\mu$g./minutes. This dose of agonist produces a submaximal (60–90% of maximum) increase in acid output in all dogs used. Pouch secretions are collected over 15 minute periods into graduated glass test-tubes and the volume measured to the nearest 0.1 ml. A 500 μl. sample is diluted with 5 ml. of saline and titrated to pH 7.0 with 100 mM. NaOH. Total acid output is computed from the product of acid concentration and volume of juice secreted. Compounds are administered intravenously (0.1 ml./kg.) via a cephalic vein or orally in a gelatin capsule when a secretory plateau (3 consecutive readings within 10%) has been attained. Secretion is measured for a period of 3 hours following administration of test compound.

The results obtained in the aminopyrine test are predictive of activity in the rat and dog tests.

No overt toxicity or side effects were noted during the rat or dog tests. The compound 4-[3-(4-[2-(2,2,2-trifluoroethyl)guanidino]pyrimid-2-ylthio)propyl]-imidazole was administered intravenously to groups of two anaesthetised rats and four conscious mice at doses which were respectively ten times and one hundred times the dose, in mg./kg., which produced an approximate 50% inhibition of gastric secretion in the anaesthetised rat. No toxic symptoms were noted in any of the dosed animals.

A number of compounds exemplified in this specification exhibit inhibition of acid secretion which shows little or no decline from peak inhibition for several hours.

According to a further feature of the invention there is provided a pharmaceutical composition which comprises a guanidine derivative of the invention in association with a non-toxic pharmaceutically-acceptable diluent or carrier.

The pharmaceutical composition may, for example, be in a form suitable for oral, rectal, parenteral or topical administration, for which purposes it may be formulated by means known to the art into the form of, for example, tablets, capsules, aqueous or oily solutions or suspension, emulsions, dispersible powders, suppositories, sterile injectable aqueous or oily solutions or suspensions, gels, creams, ointments or lotions.

In addition to the guanidine derivative of the formula I, the pharmaceutical composition of the invention for oral, rectal or parenteral administration may also contain, or be co-administered with, one or more known drugs selected from antacids, for example aluminium hydroxide - magnesium hydroxide mixtures; antipepsin compounds, for example pepstatin; other histamine H-2 antagonists, for example cimetidine or ranitidine; ulcer healing agents, for example carbenoxolone or bismuth salts; anti-inflammatory agents, f or example ibuprofen, indomethacin, naproxen or aspirin; prostaglandins, for example 16,16-dimethylprostaglandin E₂; classical antihistamines (histamine H-1 antagonists), for example mepyramine or diphenhydramine; anticholinergic agents for example atropine or propantheline bromide; anxiolytic agents, for example diazepam, chlordiazepoxide or phenobarbital.

The pharmaceutical composition of the invention for topical administration may also contain, in addition to the guanidine derivative, one or more classical antihistamines (histamine H-1 antagonists), for example mepyramine or diphenhydramine and/or one or more steroidal anti-inflammatory agents, for example fluocinolone or triancinolone.

A topical formulation may contain 1–10% w/w of the guanidine derivative of the invention. A preferred pharmaceutical composition of the invention is one suitable for oral administration in unit dosage form, for example a tablet or capsule which contains between 5 mg. and 500 mg. of the guanidine derivative, or one suitable for intravenous, subcutaneous or intramuscular injection, for example a sterile injectable containing between 0.1% and 10% w/w of the guanidine derivative.

The pharmaceutical composition of the invention will normally be administered to man for the treatment of peptic ulcers and other conditions caused or exacerbated by gastric acidity in the same general manner as that employed for cimetidine, due allowance being made in terms of dose levels for the potency and duration of action of the guanidine derivative of the present invention relative to cimetidine. Thus each patient will receive an oral dose of between 5 mg. and 500 mg., and preferably between 10 mg. and 100 mg. of guanidine derivative or an intravenous, subcutaneous or intramuscular dose of between 0.5 mg. and 50 mg., and preferably between 2 mg. and 20 mg. of the guanidine derivative, the composition being administered 1 to 4 times, and preferably once, per day. The rectal dose will be approximately the same as the oral dose. The composition may be administered less frequently when it contains an amount of guanidine derivative which is a multiple of the amount which is effective when given 1–4 times per day.

The invention is illustrated, but not limited, by the following Examples. The n.m.r. spectra are quoted in δ relative to tetramethylsilane (Δ=0) as internal standard (s=singlet, d=doublt, t=triplet, q=quartet, m=multiplet, br=broad). The temperatures are in degrees Centigrade. The following contractions are used:

HOAc=acetic acid
DMF=dimethyl formamide
ether=diethyl ether
DMSO=dimethylsulphoxide
MeOH=methanol
EtOH=ethanol
THF=tetrahydrofuran
EtOAc=ethyl acetate Attention is drawn to the fact that 3-nitropyrazole (Example 9) is an explosion hazard.

EXAMPLE 1

A mixture of (2,2,2-trifluoroethyl)isothiocyanate (0.43 g.) and 4-(4-[4-aminopyrimid-2-yl]butyl)imidazole (0.35 g.) was heated under reflux in acetonitrile for 18 hours. It was then evaporated to dryness and the residue purified by medium pressure liquid chromatography using a mixture of $CHCl_3$/MeOH/aqueous ammonia (s.g. 0.880) 15:1:0.05 v/v/v) as eluant. The appropriate fraction was evaporated to dryness and the residue of the thiourea was dissolved in concentrated ethanolic ammonia (15 ml.) and mercuric oxide (0.2 g.) added. The resulting mixture was stirred at room temperature for 30 minutes, filtered and the filtrate evaporated to dryness. The residue was dissolved in EtOH (10 ml.), treated with a small amount of hydrogen sulphide gas, filtered and the filtrate evaporated to dryness. The residue was crystallised from acetonitrile to give 4-[4-(4-[2-(2,2,2-trifluoroethyl)guanidino]pyrimid-2-yl)butyl]imidazole (0.075 g.), m.p. 191°–193°.

The 4-(4-[4-aminopyrimid-2-yl]butyl)imidazole used as starting material may be prepared as follows:

A mixture of ethyl 5-cyanovalerimidate (21 g.) and ammonium chloride (7.5 g.) in MeOH (100 ml.) was stirred overnight at room temperature and then evaporated to dryness. The residue was heated under reflux in EtOH (150 ml.) with triethylamine (56 g.) and 2-chloroacrylonitrile (36 g.). After 2 hours the mixture was evaporated to dryness and the residue was then stirred in water (300 ml.) containing sufficient HOAc to give a pH of 4. Charcoal was added and after 30 minutes the mixture was filtered and the aqueous solution extracted with EtOAc (2×150 ml.). The aqueous layer was basified with aqueous sodium hydroxide to pH 10 and extracted with EtOAc (3×150 ml.). The combined extracts were evaporated to dryness and the residue recrystallised from acetonitrile to give 2-(4-cyanobutyl)-4-aminopyrimidine.

To a mixture of 2-(4-cyanobutyl)-4-amino pyrimidine (1.9 g.) and toluene-p-thiomethylisocyanide (1.8 g.) in THF (20 ml.) was added potassium t-butoxide (2.5 g.) in THF (20 ml.). The mixture was stirred at room temperature for 2 days and then added to water (80 ml.). The pH was adjusted to 4 with HOAc and the mixture extracted with EtOAc (100 ml.). The aqueous layer was separated and the pH adjusted to 9 with sodium hydroxide and the mixture extracted with EtOAc (3×150 ml.) The combined extracts where then evaporated to dryness. The residue was heated under reflux in EtOH (200 ml.) with excess Raney nickel for 12 hours. The mixture was then cooled, filtered and evaporated to dryness. The residue was purified by medium pressure liquid chromatography using $CHCl_3$/MeOH/aqueous ammonia (s.g. 0.880) 9:1:0.05 v/v/v as eluant. The appropriate fraction was evaporated to dryness to give 4-(4-[4-aminopyrimid-2-yl]butyl)imidazole (0.4 g.). A sample converted to a hydrogen maleate had the following n.m.r. in $d_6$-DMSO: 8.65 (d,1H), 8.0 (d,1H), 7.5 (bs,2H), 7.25 (s,1H), 6.38 (d,1H), 6.03 (s,2H), 2.65 (m,4H), 1.65 (m,4H).

EXAMPLE 2

A mixture of 4-[3-(4-aminopyrimid-2-ylthio)propyl]imidazole (1.3 g.) and (2,2,2-trifluoroethyl)isothiocyanate (1 g.) was heated under reflux in acetonitrile (2 ml.) for 48 hours. The solution was cooled and the crystalline thiourea isolated by filtration. This material was dissolved in concentrated ethanolic ammonia (100 ml.) and mercuric oxide (1 g.) added. The resulting mixture was stirred at room temperature for 1 hour and then filtered. The filtrate was evaporated to dryness and the residue converted to a salt with maleic acid in EtOAc to give 4-[3-(4-[2-(2,2,2-trifluoroethyl)guanidino]pyrimid-2-ylthio)propyl]imidazole dihydrogen maleate (0.43 g.), m.p. 176°–177° (decomp.).

The 4-[3-(4-aminopyrimid-2-ylthio)propyl]imidazole used as starting material may be prepared as follows:

A mixture of thiocytosine (0.7 g.), sodium hydroxide(0.22 g.) and 4-(3-chloropropyl)imidazole (0.8 g.) was stirred in EtOH (8 ml.) and water (8 ml.) at room temperature for 16 hours and then heated under reflux for 2 hours. The solution was evaporated to dryness and the residue partitioned between dilute aqueous sodium hydroxide (20 ml.) and EtOAc (30 ml.). The EtOAc layer was evaporated to dryness to give 4-[3-(4-aminopyrimid-2-ylthio)propyl]imidazole as a brown gum which was used without further purification.

EXAMPLE 3

To a mixture of 2-(4-cyanobutyl)-4-(2-propylguanidino)pyrimidine (0.8 g.) and toluene-p-thiomethylisocyanide (0.8 g.) in THF (20 ml.) was added potassium t-butoxide (1 g.). The resulting mixture was stirred for 1 hour and then evaporated to dryness and the residue partitioned between water (50 ml.) and $CHCl_3$ (50 ml.). The organic layer was separated and evaporated to dryness. The residue was purified by medium pressure liquid chromatography using $CHCl_3$/MeOH/aqueous ammonia (s.g. 0.880) 9:1:0.05 v/v/v as eluant. The appropriate fraction was evaporated to dryness and the residue heated under reflux in EtOH (50 ml.) with excess Raney nickel. After 2 hours the mixture was filtered and the filtrate evaporated to dryness. The residue was purified by medium pressure liquid chromatography as before and the appropriate fractions evaporated to dryness. The residue on trituration with acetonitrile gave 4-[4-(4-[2-propylguanidino]pyrimid-2-yl)butyl]imidazole (0.03 g.), m.p. 172°–174°.

The 2-(4-cyanobutyl)-4-(2-propyl guanidino)pyrimidine used as starting material may be prepared as follows:

A mixture of 2-(4-cyanobutyl)-4-aminopyrimidine (1.2 g.) and propylisothiocyanate (0.9 g.) was heated under reflux in pyridine (3 ml.) for 22 hours. The mixture was then evaporated to dryness and the residue purified by medium pressure liquid chromatography using $CHCl_3$/MeOH/aqueous ammonia (s.g. 0.880) 19:1:0.05 v/v/v as eluant. The appropriate fraction was evaporated to dryness and the residue treated in concentrated ethanolic ammonia with mercuric oxide (2.2 g.). After 1 hour the mixture was filtered and the filtrate evaporated to dryness. Recrystallisation of the residue from acetone/petroleum ether (b.p. 60°–80°) gave 0.8 g. of 2-(4-cyanobutyl)-4-(2-propylguanidino)pyrimidine which was used without further purification.

EXAMPLE 4

To crude 5-[4-(2-[2,2,2-trifluoroethyl]guanidino)-pyrimid-2-yl]valeraldehyde (0.4 g.) in 50% v/v aqueous EtOH (5 ml.) was added ammonium carbonate (0.5 g.) and potassium cyanide (0.17 g.), and the mixture was heated on a steam bath at approximately 60° for 2 hours. After concentration in vacuo, water (5 ml.) was added and the mixture extracted with EtOAc (3×10 ml.). The combined extracts were evaporated in vacuo to give an oil. 2N Aqueous NaOH solution (10 ml.) was added and the basic solution extracted with EtOAc (2×10 ml.). The basic aqueous solution was brought to approximately pH 7 with 2N aqueous HCl and extracted with EtOAc. The extract was dried ($MgSO_4$) and evaporated and the residue (0.08 g.) was dissolved in a small volume of EtOH and a solution of maleic acid (0.025 g.) in EtOH (0.5 ml.) was added. On standing, 2,4-dihydroxy-5-(4-[4-(2-[2,2,2-trifluoroethyl]guanidino)pyrimid-2-yl]butyl)imidazole maleate crystallised as a colourless solid (0.07 g.), m.p. 193°–194°.

The starting material may be prepared as follows:

A mixture of 5-(4-aminopyrimid-2-yl)valeronitrile (30 g.) and 2,2,2-trifluoroethylisothiocyanate (30 g.) in acetonitrile (50 ml.) was heated under reflux for 18 hours. The mixture was then evaporated to dryness and the residue dissolved saturated methanolic ammonia. The resulting solution was stirred and mercuric oxide (48 g. added. After 2 hours the mixture was filtered through diatomaceous earth and the filtrate evaporated to dryness. The residue was triturated with ether and the solid product filtered off to give 39 g. of 5-[4-(2-[2,2,2-trifluoroethyl]guanidino)pyrimid-2-yl]valeronitrile.

A solution of 5-[4-(2-[2,2,2-trifluoroethyl]guanidino)-pyrimid-2-yl]valeronitrile (0.5 g.) in 10% v/v aqueous HOAc (10 ml.), containing lead diacetate trihydrate (0.01 g.), was hydrogenated over Raney nickel at room temperature until, by thin layer chromatography, most of the starting material had disappeared and the major product gave a positive test with 2,4-dinitrophenylhydrazine spray. The mixture was filtered, concentrated in vacuo to approximately 25 ml., brought to pH 7 with solid sodium carbonate and extracted with EtOAc. The extract was dried (MgSO$_4$) and evaporated to give approximately 0.4 g. of 5-[4-2-[2,2,2-trifluoroethyl]-guanidino)pyrimid-2-yl]valeraldehyde which was used without further purification.

EXAMPLE 5

4-[2-(2,2,2-Trifluoroethyl)guanidino]-2-methylsulphinyl pyrimidine (168 mg.) was added to a stirred mixture of 4-hydroxy-6-(2-hydroxyethyl)-2-methylpyrimidine (130 mg.), a 50% w/w dispersion of sodium hydride in oil (96 mg.) and t-butanol (10 ml.) at 50°, and the resulting mixture stirred at 50° for 3 hours. The mixture was evaporated to dryness, and the residue was partitioned between water and EtOAc. The aqueous phase was acidified to pH 1 and washed with EtOAc and then neutralised with sodium bicarbonate and extracted with EtOAc. The EtOAc extract was dried and evaporated to dryness and the residue dissolved in acetone, and the solution was added to a solution of maleic acid in acetone. The precipitate was collected and crystallised from aqueous EtOH to give 4-hydroxy-2-methyl-6-[2-(4-[2-(2,2,2-trifluoroethyl)guanidino]pyrimid-2-yloxy)ethyl]pyrimidine hydrogen maleate (125 mg.), m.p. 197°–200°.

The 4-hydroxy-6-(2-hydroxyethyl)-2-methylpyrimidine used as starting material may be prepared as follows:

A solution of ethyl (4-hydroxy-2-methylpyrimid-6-yl)acetate (0.38 g.) in isopropanol (10 ml.) was heated under reflux and treated with sodium borohydride (0.2 g.). The mixture was heated under reflux for 4 hours with the addition of two further portions (0.1 g.) of sodium borohydride after 2 and 3 hours. The mixture was evaporated to dryness and the residue was partitioned between water and ether. The aqueous phase was acidifed with HOAc and then extracted with EtOAc in a continuous extractor for 24 hours. The extract was dried and then evaporated to dryness to give 4-hydroxy-6-(2-hydroxyethyl)-2-methylpyrimidine (0.15 g.) which was used without further purification.

EXAMPLE 6

A mixture of 4-[2-(2,2,2-trifluoroethyl)guanidino]-2-(3-hydroxypropoxy)pyrimidine (293 mg.), a 50% w/w dispersion of sodium hydride in oil (72 mg.) and t-butanol (5 ml.) was stirred at 50° for 0.5 hours and then treated with 2,6-dichloropyrazine (165 mg.) and the resulting mixture was stirred at 50° for 18 hours. The mixture was evaporated to dryness and the residue stirred with a mixture of N aqueous hydrochloric acid and ether. The insoluble white solid was collected to give 6-chloro-2-[3-(4-[2-(2,2,2-trifluoroethyl)-guanidino]-pyrimid-2-yloxy)propoxy]pyrazine hydrochloride (70 mg.), m.p. 167°–169°.

The starting material may be prepared as follows:

A 50% w/w dispersion of sodium hydride in oil (48 mg.) was added to propane-1,3-diol (0.5 ml.) and the mixture stirred at room temperature for 0.5 hours. 4-[2-(2,2,2-Trifluoroethyl)guanidino]-2-methanesulphonylpyrimidine (0.15 g.) was added and the mixture heated at 90° with occasional shaking for 0.5 hours and then cooled to room temperature. The mixture was taken up in N aqueous HCl and washed with EtOAc. The aqueous phase was basified with 10N aqueous NaOH and then extracted three times with EtOAc. The combined extracts were dried and evaporated to dryness. A solution of the residue in acetone was added to a solution of maleic acid in acetone, and the precipitate collected to give 4-[2-(2,2,2-trifluoroethyl)guanidino]-2-(3-hydroxypropoxy)pyrimidine hydrogen maleate (0.19 g.), m.p. 165°–166° (after recrystallisation from EtOH).

EXAMPLE 7

4-[2-(2,2,2-Trifluoroethyl)guanidino]-2-methylsulphinylpyrimidine (150 mg.) was added to a stirred mixture of 2-(3-hydroxypropyl)pyridine (82 mg.), a 50% w/w dispersion of sodium hydride in oil (30 mg.) and DMF (2 ml.) and the mixture heated at 90° for 1 hour. The mixture was evaporated to dryness and the residue partitioned between water and EtOAc. The EtOAc phase was dried and evaporated to dryness. The residue was subjected to preparative thin layer chromatography using EtOAc/MeOH/aqueous ammonia (s.g. 0.88) 6:1:0.5 v/v/v as developing solvent. The band having Rf 0.6 was eluted with MeOH and the MeOH evaporated to dryness to give 2-[3-(4-[2-(2,2,2-trifluoroethyl)-guanidino]-pyrimid-2-yloxy)propyl]pyridine (45 mg.), which was characterised as the bis hydrogen maleate salt, m.p. 118°–120° (after crystallisation from acetone/ether).

EXAMPLE 8

Sodium hydride (46 mg. of a 61% w/w dispersion in oil) was added to a hot solution of 1-(4-hydroxybutyl)-3-[2-(2,2,2-trifluoroethyl)guanidino]pyrazole (279 mg.) in dry t-butanol (10 ml.). 2,6-Dichloropyrazine (180 mg.) was added and the mixture was stirred at room temperature for two hours, followed by evaporation in vacuo to dryness. The residue was treated with dilute aqueous 0.5N HCl (10 ml.), and then extracted with EtOAc (4×10 ml.). The combined extracts were dried (MgSO$_4$) and evaporated. The residue was purified by preparative t.l.c. on silica gel plates using triethylamine/EtOH/EtOAc 1:1:9 v/v/v as developing solvent to give 2-chloro-6-[4-(3-[2-(2,2,2-trifluoroethyl)-guanidino]pyrazol-1-yl)butoxy]pyrazine (170 mg.; 43%) having the following n.m.r. in d$_6$DMSO: 8.25 (s, 2H); 7.4 (d, 1H); 5.6 (d, 1H); 4.25 (t, 2H); 3.9 (m, 4H); 1.7 (br m, 4H).

The starting material may be prepared as follows:

2-Chloroacrylonitrile (12.2 g.) was added slowly to a mixture of 4-hydroxybutylhydrazine (16.1 g.) in water (60 ml.) containing potassium carbonate (21.2 g.). After the resulting exotherm has subsided, the reaction mixture was stirred at room temperature for 3 hours, then extracted continuously with ether for 3 days. On evaporation of the ether in vacuo 3-amino-1-(4-hydroxybutyl)pyrazole was obtained as a thick brown oil (96% yield).

To a solution of 3-amino-1-(4-hydroxybutyl)pyrazole (22 g.) in dry acetonitrile (60 ml.) was slowly added 2,2,2-trifluoroethylisothiocyanate (20.9 g.) over 5 minutes. After stirring for 17 hours the solvent was evaporated in vacuo and the residue was purified by column chromatography on silica gel using EtOAc as eluant to give 1-(4-hydroxybutyl)-3-(3-[2,2,2-trifluoroethyl]thioureido)pyrazole (38%), m.p. 94°–96° [after recrystallisation from petroleum ether (b.p. 40°–60°)].

Mercuric oxide (30.1 g.) was added quickly to a stirred solution of 1-(4-hydroxybutyl)-3-(3-[2,2,2-trifluoroethyl]thioureido)pyrazole (10.4 g.) in methanolic ammonia (5N., 340 ml.). After stirring for 3 hours at room temperature, the mixture was filtered through a pad of diatomaceous earth and the filtrate was evaporated in vacuo to give 1-(4-hydroxybutyl)-3-[2-(2,2,2-trifluoroethyl)guanidino]pyrazole, m.p. 105°–106° (yield 82%).

EXAMPLE 9

To a stirred mixture of 4-[3-(2-[2,2,2-trifluoroethyl]-guanidino)pyrazol-1-yl]valeronitrile (1 g.) and toluene-p-thiomethylisocyanide (1.7 g.) in THF (20 ml.) was added potassium t-butoxide (1.6 g.). After 1 hour the mixture was added to water (50 ml.) and the pH was adjusted to 7 with HOAc. The mixture was then extracted with EtOAc (30 ml.), the extract evaporated to dryness and the residue purified by medium pressure liquid chromatography using chloroform/MeOH-/aqueous ammonia (s.g. 0.880) 15:1:0.05 v/v/v as eluant. The appropriate fractions were combined and evaporated to dryness and the residue heated under reflux in EtOH (15 ml.) with Raney nickel (2 g.) for 1 hour. The mixture was then filtered and hydrogen sulphide gas was passed briefly into the solution which was then filtered again. The filtrate was evaporated to dryness to give 0.12 g. of 4-[4-(3-[2-(2,2,2-trifluoroethyl)-guanidino]pyrazol-1-yl)butyl]imidazole (yield 10%). The n.m.r. spectrum in $d_6$DMSO contained the following resonances: 1.7 (m, 4H); 2.6 (m, hidden by solvent); 4.0 (t, 2H); 4.2 (q, 2H); 6.7 (s, 1H); 6.8 (d, 1H); 7.5 (d, 1H); 7.6 (s, 1H).

The starting material may be prepared as follows:

Sodium hydride paste (6.16 g. of 61% w/w suspension in liquid paraffin) was added portionwise over 30 minutes to a solution of 3-nitropyrazole (17.4 g.) in dry DMF (150 ml.) with external ice cooling to maintain the temperature at 20°–30°. The mixture was stirred for 45 minutes and to the almost clear solution was added 5-bromovaleronitrile (25 g.) over 30 minutes, at 25°–30°, and the mixture was stirred for 4 hours. Water (450 ml.) and EtOAc (450 ml.) were added and the upper layer was separated, dried (MgSO$_4$) and evaporated in vacuo to an oil which was a mixture of 5-(3-nitropyrazol-1-yl)valeronitrile and 5-(5-nitropyrazol-1-yl)valeronitrile. The oil was divided into two 15 g. portions which were fractionated on a silica column (3.5 cm diameter×100 cm long) eluted at 2 atmospheres by EtOAc/60°–80° petroleum ether (3:7 v/v). The 1,5 isomer was eluted first followed by the 1,3 isomer. The 5-(3-nitropyrazol-1-yl)valeronitrile had m.p. 32°–33°.

To a solution of 5-(3-nitropyrazol-1-yl)valeronitrile (9.16 g.) in dry THF (200 ml.) was added 5% w/w palladium on carbon (1.8 g.). The mixture was stirred at 20° under an atmosphere of hydrogen. 3.2 Liters of hydrogen were absorbed over 4 hours. The catalyst was filtered off and the filtrate was evaporated in vacuo to give 5-(3-aminopyrazol-1-yl)valeronitrile as an oil.

To a solution of 5-(3-aminopyrazol-1-yl)valeronitrile (7.0 g.) in acetonitrile (25 ml.) was added 2,2,2-trifluoroethylisothiocyanate (6.02 g.). After 15 minutes the solvent was evaporated in vacuo to give 5-(3-[3-(2,2,2-trifluoroethyl)thioureido]pyrazol-1-yl)valeronitrile as a white crystalline solid, m.p. 96°–98°.

The above thiourea (12.5 g.) was dissolved in 8M ammonia in ethanol (120 ml.). Mercuric oxide (12.8 g.) was added and the mixture was stirred at 20° for 30 minutes. The resulting mixture was filtered and the filtrate was evaporated in vacuo to give 5-[3-(2-[2,2,2-trifluoroethyl]guanidino)pyrazol-1-yl]valeronitrile as an oil. A sample of the oil was dissolved in acetone and 5 molecular equivalents of maleic acid were added. Ether was added to the resulting clear solution to produce the crystalline maleate, m.p. 123°–125°.

EXAMPLE 10

The process of Example 3 was repeated using 2-(5-cyanopentyl)-4-aminopyrimidine in place of 2-(4-cyanobutyl)-4-aminopyrimidine and 2,2,2-trifluoroethylisothiocyanate in place of propylisothiocyanate to give 4-[5-(4-[2-(2,2,2-trifluoroethyl)guanidino]pyrimid-2-yl)pentyl]imidazole dioxalate, m.p. 185°–190° (yield 6%).

EXAMPLE 11

A tablet containing 50 mg. of 4-[4-(4-[2-(2,2,2-trifluoroethyl)guanidino]pyrimid-2-yl)butyl]imidazole may be prepared using ingredients in the following proportions:

|     | Tablet Core                   | mg./tablet |
| --- | ----------------------------- | ---------- |
| (a) | Active agent                  | 50         |
|     | Lactose                       | 218.5      |
|     | Calcium carboxymethylcellulose| 22.5       |
|     | Polyvinylpyrrolidone          | 6.0        |
|     | Magnesium stearate            | 3.0        |
| (b) | Hydroxypropylmethylcellulose  | 4.5        |
|     | Polyethylene glycol           | 0.9        |
|     | Titanium dioxide              | 1.35       |

The active agent, lactose and calcium carboxymethylcellulose are mixed. An aqueous solution of polyvinylpyrrolidone is added, and the mass is then mixed until it is suitable for granulation. The mass is then granulated and dried. The magnesium stearate is blended with the dried granules and the resulting mixture is compressed into tablets. The tablets are film-coated using an aqueous or solvent suspension of hydroxypropylmethylcellulose, polyethylene glycol and titanium dioxide.

We claim:

1. A guanidine derivative of the formula I:

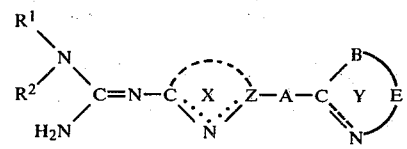

in which

R$^1$ and R$^2$, which may be the same or different, are hydrogen, or branched or unbranched 1–10C alkyl, 3–8C cycloalkyl or 4–14C cycloalkylalkyls, each alkyl, cycloalkyl or cycloalkylalkyl being optionally substituted by one or more halogens selected from fluorine, chlorine and bromine provided that at least one of R$^1$ and R$^2$ is a halogen-substituted alkyl, cycloalkyl or cycloalkylalkyl and provided that there is no halogen on the carbon of the alkyl, cycloalkyl or cylcloalkylalkyl which is directly attached to the nitrogen;

in ring X the dotted line is a double bond on one side of the nitrogen and Z is carbon or nitrogen such that ring X is 6-membered aromatic heterocyclic ring which contains at least one nitrogen and may optionally contain one or two additional hetero atoms selected from oxygen, nitrogen and sulphur, wherein that ring is selected from pyrazine, pyridine, pyrimidine and 1,3,5-triazine, which heterocyclic ring may, where possible, carry one or two optional substituents, the optional substituents on ring X being selected from fluorine, chlorine, bromine, 1–6C alkyl, 1–6C alkyl, 1–6C alkoxy, 1–6C alkylthio, trifluoromethyl, hydroxy and amino;

—A— is a 1–8C alkylene chain which is optionally substituted by one or two 1–3C alkyls and into which is optionally inserted, as part of the backbone of the chain, NH or 1–6C N-alkyl or one or two groups selected from oxygen, sulphur, cis and trans vinylene, ethynylene, phenylene and 5–7C, alkylene provided that no two insertions selected from oxygen and sulphur are directly attached one to the other, and provided that when an optional insertion is made in chain A which results in the inserted group being directly attached to ring Y the inserted group is other than NH or N-alkyl; or —A— is 5–7C cycloalkylene or phenylene;

ring Y is of the formula IV, V, VI, VII, VIII, IX, X, XI, XII, XIII, XIV, XV or XVII:

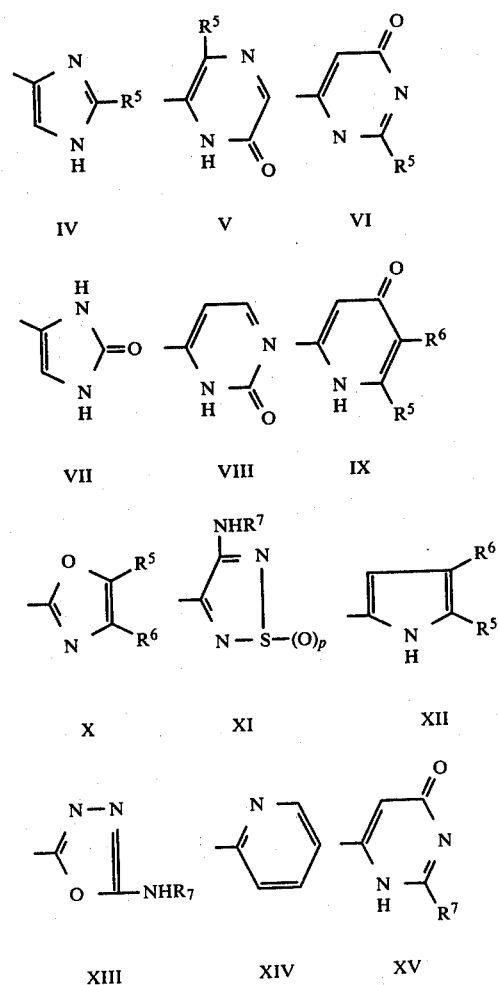
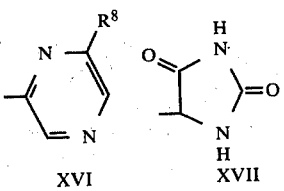

in which
R$^5$ is hydrogen or of the formula NHR$^7$, R$^6$ is hydrogen, cyano, nitro, methoxycarbonyl, carbamoyl, methylcarbamoyl or dimethylcarbamoyl, R$^7$ is hydrogen or methly, R$^8$ is hydrogen, chlorine or bromine and p is 1 or 2:

and the pharmaceutically-acceptable acid-addition salts thereof.

2. A guanidine derivative of the formula I given in claim 22 in which R$^1$ and R$^2$ are selected from the group consisting of hydrogen, 2,2,2-trifluoroethyl, 2,2,2-trichloroethyl, 2-chloro-2,2-difluoroethyl, 2,2-dichloro-2-fluoroethyl, 2-bromo-2,2-difluoroethyl, 2,2-dibromo-2-fluoroethyl, 2-fluoroethyl, 2-chloroethyl, 2,2-difluoroethyl, 2,2-dichloroethyl, 2-chloro-2-fluoroethyl, 2-bromo-2-fluoroethyl, 2,2,3,3,-tetrafluoropropyl, 2,2,3,3,3-pentafluoropropyl, 1,1,1,3,3,3-hexafluoroisopropyl, 1,3-dichloro-1,1,3,3-tetrafluoroisopropyl, 1-chloro-1,1,3,3-pentafluoroisopropyl, 1,3-difluoroisopropyl, 2,2,3,3,4,4,4-heptafluorobutyl, 2,2,3,3-tetrafluorocyclopropyl, 2-chloro-2,3,3-trifluorocyclopropyl, 2,2-difluorocyclopropyl, 2-chloro-3,3-difluorocyclopropyl, 2,2,3,3,4,4-hexafluorocyclobutyl, 2-chloro-2,3,3,4,4-pentafluorocyclobutyl, (1,2,2,3,3-pentafluorocyclopropyl)methyl, (2-chloro-1,2,3,3-tetrafluorocyclopropyl)methyl, (1,2,2,3,3,4,4-heptafluorocyclobutyl)methyl, (2-chloro-1,2,3,3,4,4-hexafluorocylcobutyl)methyl, methyl, ethyl, propyl, isopropyl, butyl, cyclobutyl, cyclopropylmethyl and cyclobutylmethyl, provided that at least one of R$^1$ and R$^2$ is halogen-substituted, in ring X the optional substitutes are selected from fluorine, chlorine, bromine, methyl, methoxy, methylthio, trifluoromethyl, hydroxy and amino;
—A— is phenylene, cyclopentylene, cyclohexylene, trimethylene, tetramethylene, pentamethylene, thioethylene, thiotrimethylene, thiotetramethylene, thiopentamethylene, oxyethylene, oxytrimethylene, oxytetramethylene, methylenethiomethylene, methylenethioethylene, methylenethiopropylene, methyleneoxymethylene, methyleneoxyethylene, ethyleneoxyethylene, oxy-2-methylethylene, thiopropylenethiomethylene, oxypropyleneoxy, oxyethyleneoxymethylene, oxyethylenethio, oxypropylenethio, iminoethylene, iminopropylene, vinylenepropylene, oxymethylenevinylene, 1,3-phenylene, 1,3-cyclopentylene, methylene-1,4-phenylene, ethyleneoxymethylene-1,4-phenylene, oxy-1,3-phenylenemethylene, thiomethyleneethynylenemethylene or tetramethyleneoxy;
and the pharmaceutically-acceptable acid-addition salts thereof.

3. A guanidine derivative as claimed in claim 22 in which ring Y is of the formula IV, V, VI, VII, VIII, IX, X, XI, XII or XIII given in claim 13 in which R$^5$ is hydrogen or of the formula NHR$^7$, R$^6$ is hydrogen, cyano, nitro, methoxycarbonyl, carbamoyl, methylcarbamoyl or dimethylcarbamoyl, $R^7$ is hydrogen or methyl and p is 1 or 2.

4. A guanidine derivative as claimed in claim 13 in which $R^2$ is a hydrogen, $R^1$ is 2,2,2-trifluoroethyl and ring X carries no optional substituent.

5. A guanidine derivative as claimed in claim 3 in which ring X is pyrimidine in which A is linked at the 2-position.

6. A guanidine derivative as claimed in claim 4 in which ring Y is of the formula IV given in claim 13 in which $R^5$ is hydrogen, amino or methylamino.

7. A guanidine derivative as claimed in claim 5 in which ring X is pyrimidine in which A is linked at the 2-position and A is a tetramethylene or thiotrimethylene.

8. A guanidine derivative selected from the group consisting of 4-[4-(4-[2-(2,2,2-trifluoroethyl)guanidino]-pyrimid-2-yl)butyl]imidazole, 4-[3-(4-[2-(2,2,2-trifluoroethyl)guanidino]pyrimid-2-ylthio)propyl]imidazole, and the pharmaceutically-acceptable acid-addition salts thereof 9. A pharmaceutical composition comprising a guanidine derivative as claimed in claim 22 in an amount effective to inhibit gastric acid secretion in a warm-blooded animal and in association with a pharmaceutically-acceptable diluent or carrier.

10. A method of inhibiting gastric acid secretion in a warm-blooded animal which comprises administering to the animal an effective amount of a compound of claim 22.

* * * * *